United States Patent [19]

McGredy

[11] Plant 4,612

[45] Jan. 6, 1981

[54] ROSE PLANT

[76] Inventor: Samuel D. McGredy, P.O. Box 14-100, Auckland, New Zealand

[21] Appl. No.: 47,939

[22] Filed: Jun. 12, 1979

[51] Int. Cl.[3] ..... A01H 5/00

[52] U.S. Cl. ..... Plt./3

[58] Field of Search ..... Plt./3, 8

*Primary Examiner*—Robert E. Bagwill

*Attorney, Agent, or Firm*—Vincent G. Gioia

[57] ABSTRACT

A new white miniature rose with pointed buds of petite size.

1 Drawing Figure

The present invention relates to a new and distinct variety of rose plant of the miniature rose class, which was originated by my crossing as seed parent the rose known as "New Penny" and the rose known as "Temple Bells" as pollen parent.

Among the novel characteristics possessed by this new variety which distinguish it from its parents and all other varieties of which I am aware are: Classic pointed buds, pure white coloring and petite size and a low growing but spreading plant. Asexual reproduction by budding of the new variety as performed in Clackamas County, Oreg., shows that the foregoing and other distinguishing characteristics come true to form and are established and transmitted through succeeding propagations.

The new and improved rose variety which I have developed is a fine miniature rose producing large numbers of flowers of clean white coloring, both singly-borne and in sprays. The flower begins with classic, tapered bud form and maintains its pure white coloring as it opens and upon aging. The plant is low growing but is spreading and can be used where a creeping and crawling ability is advantageous. It also exhibits unusually superior resistance to disease.

The accompanying drawing shows typical specimens of the vegetative growth and flowers of the new variety in different stages of development and as depicted in color as nearly true as it is reasonably possible to make the same in color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "149C" is plate 149C of the Royal Horticultural Society Color Chart.

Parentage: Seedling.

*Seed parent.*—"New Penny".

*Pollen parent.*—"Temple Bells".

Class: Miniature.

The following observations are made of specimens grown in a greenhouse in Clackamas County, Oreg. during the month of March.

1. FLOWER

Blooming habit: Recurrent.

A. Bud:

(1) *Size.*—Petite, 8 to 10 mm.

(2) *Form.*—Pointed.

(3) *Color.*—When sepals first divide — white. When petals being to unfurl — pure white. Reverse side of petals — pure white.

(4) *Sepals.*—Longer than bud, fancy, lightly pilose but heavily pilose on margins.

(5) *Peduncle.*—Length — 15 to 20 mm. Aspect — straight. Strength — erect. Color — yellow-green 149C.

B. Bloom:

(1) *Size.*—Average size when fully expanded — about 25 mm.

(2) *Borne.*—Singly and in sprays.

(3) *Form.*—High centered at first, opening quickly to loose open blooms.

(4) *Petalage.*—Number of petals under normal conditions — about 24 to 28.

(5) *Color.*—(During first two days). Upper surface of petals — white. Base of petals (point of attachment) — 149D. Underside of petals — white. General tonality from a distance — rich white.

(6) *Color change.*—Almost no color change as bloom ages, maintaining white coloring as bloom ages even after three or more days.

C. Petals:

(1) *Texture.*—Medium.

(2) *Appearance.*—Inside — satiny.

(3) *Form.*—Loose, open.

(4) *Arrangement.*—Regularly arranged.

(5) *Petaloids in center.*—Few.

(6) *Persistence.*—Drop off cleanly.

(7) *Fragrance.*—Slight tea fragrance.

(8) *Lasting quality.*—Long lasting on plant, impractical as cut flower.

2. REPRODUCTIVE ORGANS

A. Stamens, filaments and anthers:

(1) *Arrangement.*—Filaments incurved, yelow--green 150C. Stamens regularly arranged around styles but with uneven length, slightly incurved.

(2) *Color.*—17A.

B. Pollen: Color — 17B.

C. Styles: Bunched, then sinuous, color 150D.

D. Stigmas: Almost clear suffused with 150D.

E. Hips: Oval with 5 to 8 carpels, 4 to 6 mm, orange red 33A, seeds enclosed.

3. PLANT

A. Form: Low growing, spreading.

B. Growth: Vigorous, densely branching.

*Height attained.*—8 to 10 inches (20-25 cm).

C. Foliage: Compound 5 to 9 leaflet leaves.

(1) *Size.*—Tiny, 6 to 12 mm.

(2) *Quantity.*—Very abundant.

(3) *Color.*—New foliage: Upper side — near to 144B. Under side — near to 144B. Old foliage: Upper side — 141B. Under side — 143B.

(4) *Shape.*—Long, pointed, acuminate.

(5) *Texture.*—Upper side — shiny. Under side — matte.

(6) *Edge.*—Serrated.

(7) *Serration.*—Simple, tipped reddish.

(8) *Leaf stem.*—Color — near to 34C. Under side — 141B.

(9) *Stipules.*—Long, i.e., ½ length to first leaflets, are bearded.

(10) *Resistance to disease.*—Blackspot — excellent. Mildew — excellent. Rust — excellent.

D. Wood:

(1) *New wood.*—Color — near to 146C. Bark — smooth.

(2) *Old wood.*—Color — near to 146B. Bark — smooth.

E. Thorns:

(1) *Thorns.*—Quantity: Few. On laterals from stalk — few. Form — long, recurved. Length — 2 to 3 mm. Color (when young) — 65A tipped whitish. Position — irregular, few.

(2) *Prickles.*—None.

F. Winter hardiness: Winter hardy.

I claim:

1. A new and distinct variety of rose plant of the miniature class, substantially as shown and described, characterized particularly by petite pointed buds opening into pure white maintaining their color well upon aging and a loose growing, spreading plant that is very resistant to blackspot, mildew and rust.

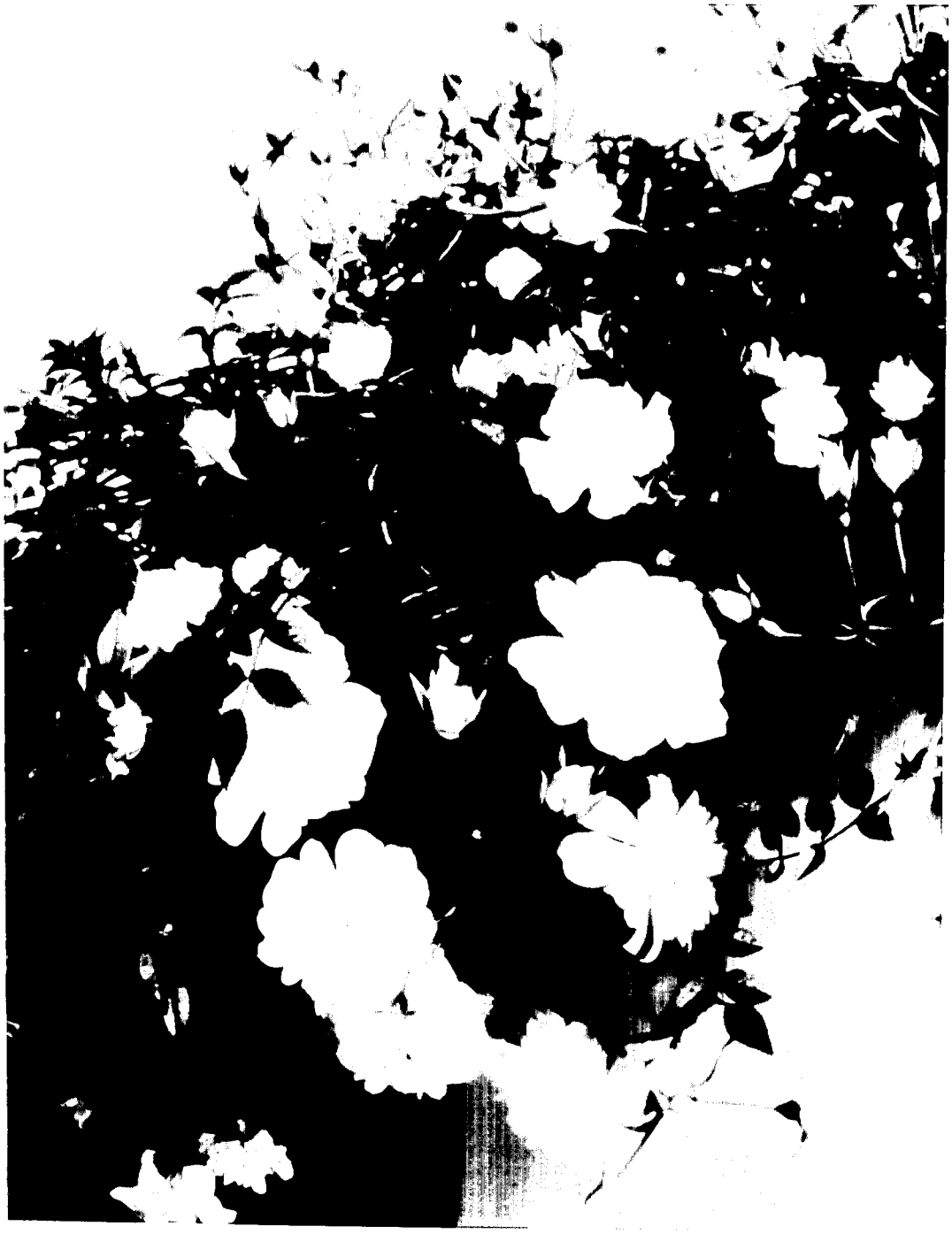

* * * * *